United States Patent [19]

Besocke et al.

[11] 4,409,509

[45] Oct. 11, 1983

[54] PIEZOELECTRICALLY DRIVEN TRANSDUCER FOR ELECTRON WORK FUNCTION AND CONTACT POTENTIAL MEASUREMENTS

[75] Inventors: Karl-Heinz Besocke, Jülich; Siegfried Berger, Titz-Rödingen, both of Fed. Rep. of Germany

[73] Assignee: Kernforschungsanlage Jülich GmbH, Jülich, Fed. Rep. of Germany

[21] Appl. No.: 302,233

[22] Filed: Sep. 14, 1981

[30] Foreign Application Priority Data

Sep. 12, 1981 [DE]  Fed. Rep. of Germany ....... 3034390

[51] Int. Cl.³ ............................................. H01L 41/10
[52] U.S. Cl. .................................... 310/317; 310/321; 361/289
[58] Field of Search ............... 310/317, 321, 330, 331, 310/332, 328; 307/2; 361/289, 292

[56] References Cited

U.S. PATENT DOCUMENTS

| 3,093,783 | 6/1963 | Hass | 307/2 X |
| 3,218,636 | 11/1965 | Bernstein et al. | 310/321 X |
| 3,515,890 | 6/1970 | Kohashi et al. | 307/2 |
| 3,611,127 | 10/1971 | Vosteen | 361/289 X |
| 3,949,246 | 4/1976 | Lohrmann | 361/289 X |
| 4,100,442 | 7/1978 | Besocke | 310/321 X |
| 4,156,150 | 5/1979 | Harrigan et al. | 307/2 |

FOREIGN PATENT DOCUMENTS 1542837 3/1979 United Kingdom .
1568634 6/1980 United Kingdom .

OTHER PUBLICATIONS

"Halbleiter-Schaltungstechnik" by Tietze and Schenk, 1974.

Primary Examiner—William M. Shoop
Assistant Examiner—Peter S. Wong
Attorney, Agent, or Firm—Frishauf, Holtz, Goodman & Woodward

[57] ABSTRACT

The resonance of a piezoelectric vibrating element itself sets the frequency of the excitation producing ac oscillator for e.g. Kelvin probe or chopper applications.

The oscillation amplitude is continuously adjustable. The superposition of a dc voltage in addition to the ac excitation voltage renders a continuously adjustment of the mean spacing of the working electrodes. A phase stable reference signal is provided for phase sensitive amplifier synchronization.

3 Claims, 2 Drawing Figures

PIEZOELECTRICALLY DRIVEN TRANSDUCER FOR ELECTRON WORK FUNCTION AND CONTACT POTENTIAL MEASUREMENTS

The invention concerns a piezoelectrically driven transducer for measuring contact potentials between electrodes movable relative to each other and likewise measuring electron work functions of surfaces. In particular it concerns apparatus in which an oscillatory exciting voltage drives an element of piezoelectric material carrying an oscillating electrode which is mounted on a spring, while a controllable voltage is superimposed upon the oscillating voltage for variation of the mean spacing between the oscillatory electrode and a counterelectrode.

A piezoelectric device of this kind is disclosed in U.S. Pat. No. 4,100,442. It is described as a Kelvin probe for the determination of electron work functions relating to the movement of electrons out of the boundary surface of a material. The electron work function is of importance for the determination of surface properties of materials. Such piezoelectric transducers, in addition to their application as Kelvin probes, are also usable for the modulation of optical transmissivity of an optical path.

In the known transducers an excitation circuit for the piezoelectric material is provided with a transformer and a sinewave generator as an ac source. For setting the mean spacing of the electrodes that are moving together and apart a dc voltage source is superimposed to the ac driving voltage. There is the disadvantage that for excitation of the transducer at a resonant frequency, tuning the sine wave generator must be performed with great precision. Furthermore, when the resonant frequency changes, for example as a result of temperature changes or aging of the piezoelectric material, the frequency of the sine wave generator must be made to follow these changes and phase-balancing must be performed anew.

SUMMARY OF THE INVENTION

It is an object of this invention to provide a simple and self-regulating drive for the piezoelectric element with operation of the latter at its resonant frequency, while the measured values are ascertainable without interference. It is a further object that the setting of the mean spacing between the electrodes in relative movement should be decoupled from the excitation of the oscillations of the element. Finally, independent manipulation of the individual control magnitudes is to be obtained.

Briefly, the oscillations are produced by a self-excitation circuit, which is to say that the resonant frequency of the transducer itself determines the frequency of excitation. A capacitor connects one terminal of the piezoelectric component to the oscillation circuit while the other pole of the piezoelectric element is connected to the reference potential, which may be grounded potential. A controllable dc voltage is applied in parallel to the terminals of the piezoelectric element for varying the mean electrode spacing. In this manner self-excitation of the transducer at resonant frequencies, independent of the additional dc voltage superimposed on the excitation voltage, is obtained and the desired resonant frequencies (fundamental or harmonics) are automatically set. The excitation circuit in addition is provided with a control circuit for varying the amplitude of oscillation.

Preferably the excitation circuit comprises an operational amplifier having its inverting input connected to an inverse feedback circuit branch and its non-inverting input connected to a positive feedback circuit branch. The pole of the piezoelectric element connected with the oscillation circuit is connected by a capacitor connected between the inverting input of the operational amplifier and the piezoelectric element.

In order to make possible the provision of a continuous change of the amplitude of the transducer, a controllable regulated supply voltage is applied to the operational amplifier. The amplitude can thus, just like the average spacing of the electrodes, be adjusted without substantial influence on the oscillation properties of the exciting circuit.

BRIEF DESCRIPTION OF THE DRAWINGS

The invention is further described by way of illustrative example with reference to the annexed drawings, in which.

DESCRIPTION OF THE ILLUSTRATED EMBODIMENT

Figure 1:
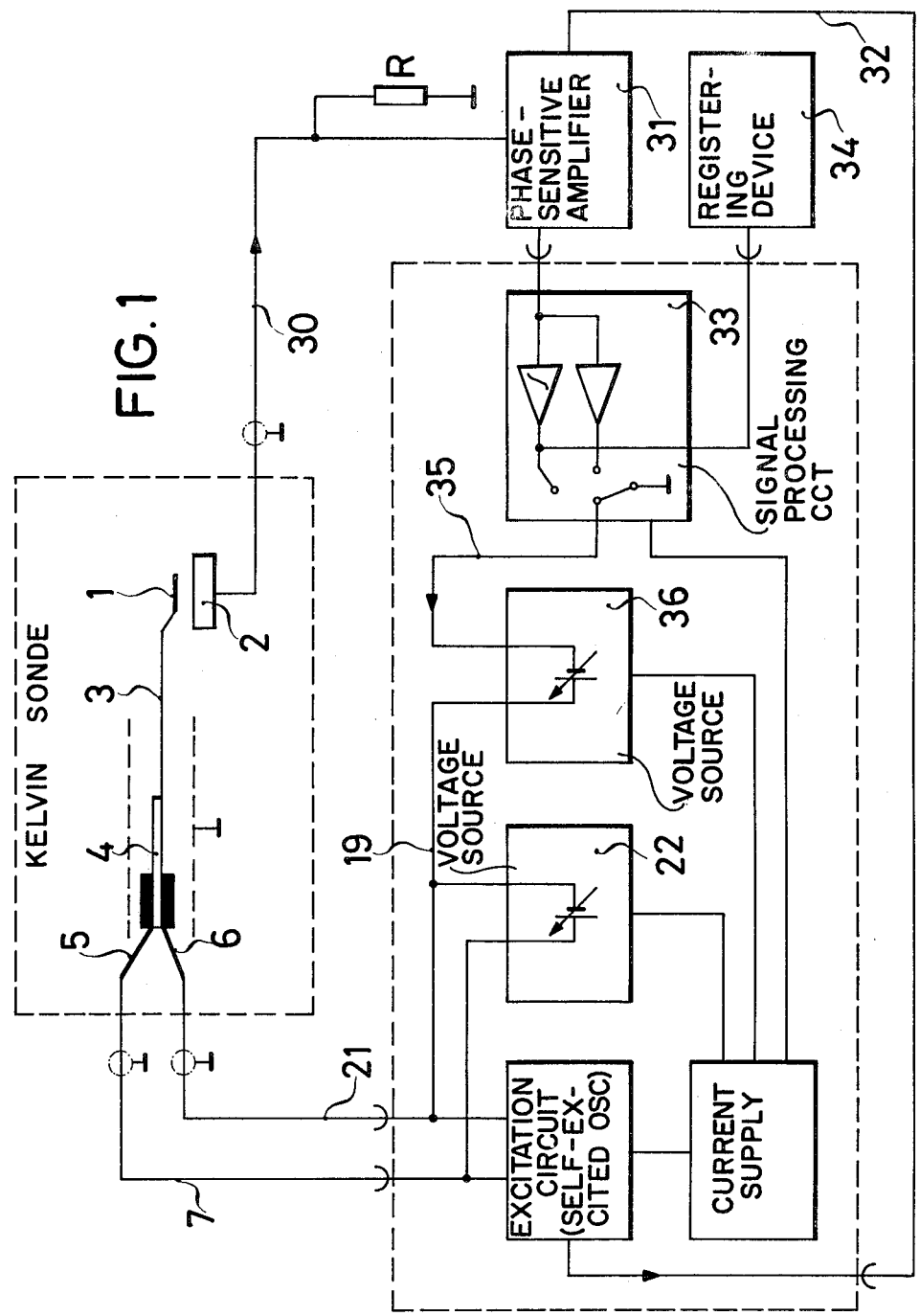
FIG. 1 is a block diagram showing the operation of the piezoelectric transducer of the present invention as a Kelvin probe.

As shown in FIG. 1 the piezoelectric transducer has an oscillatory electrode 1 and a counter-electrode 2, the latter being in the illustrated case in fixed position. For the use of the transducer as a Kelvin probe, the oscillating electrode 1 is a reference electrode and consists of a material of which the work function does not change during the measurement, for example gold. The counter-electrode 2 is the sample of material that is to be measured. The oscillatory electrode 1 is mounted on a leaf-spring 3 that at its other end is excited into transverse oscillations by a body of piezoelectric material 4. Instead of a leaf-spring other spring elements, particularly longitudinal vibrators, are usable. The illustrated element 3 is made of molybdenum.

The piezoelectric material 4 connected with the spring 3, constituted as a piezoceramic wafer 0.1 mm thick, is coated on both sides with a metallic layer and has terminals (poles) 5 and 6 for the connection of electrical conductors. A piezoceramic wafer of barium/-lead-zirconate/titanate is preferably used because it is a piezoceramic material that is capable of withstanding the effects of temperature and of ultra-high vacuum.

Figure 2:
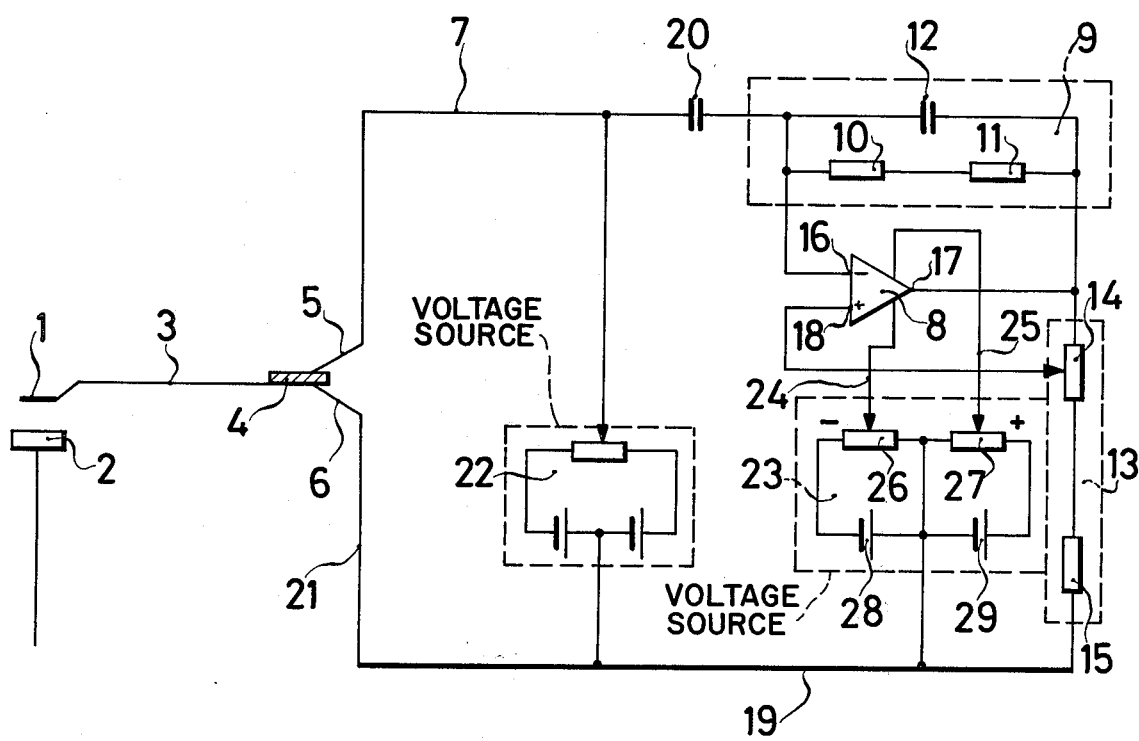
FIG. 2 is a circuit diagram of an excitation circuit with provision for electrode spacing and amplitude controls.

An electrical connection 7 leads from the terminal 5 on the piezoelectric element to the exciting circuit driving the piezoelectric element. The exciter circuit consists (see FIG. 2) of an operational amplifier 8, an inverse feedback circuit 9 having resistors 10 and 11 and a capcitor 12 connected in parallel thereto, and also a positive feedback circuit 13 composed of the variable resistor 14 and the fixed resistor 15. The inverse feedback circuit 9 is connected between the inverting input 16 and the output 17 of the operational amplifier 8, while the positive feedback circuit 13 is connected to the non-inverting input 18. The resistor 15 of the positive feedback circuit is connected to the reference or ground potential conductor 19 and the resistor 14 is connected to the output 17 of the operational amplifier 8. The conductor 7 that is connected to the terminal 5 of the piezoelectric element 4 leads to a capacitor 20, the other terminal of which is connected to the inverting input 16 of the operational amplifier 8, while the terminal 6 of the piezoelectric element 4 is connected by the conductor 21 to the ground or reference potential conductor 19.

The resistance values of the resistors 10, 11, 14, and 15, as well as the capacitances of the capacitors 12 and 20 are so selected that with taking account of the electrical characteristics of the piezoelectric oscillating element, optimum impedance conditions for the exciting circuit are provided. The extent of positive feedback of the circuit is adjustable by means of the variable resistor 14.

A controllable voltage source 22 is connected to the two terminals 5 and 6 of the piezoelectric element, so that a voltage for setting the mean spacing between the oscillating electrode 1 and the counter-electrode 2 can be superimposed upon the excitation voltage provided by the excitation circuit. In the illustrated example a regulated dc voltage source is used that is manually adjustable to set the voltage. Instead thereof, of course, an automatically operating regulation circuit for automatic electrode spacing or an arc generator for double modulation for the oscillating element can be provided.

The operational amplifier 8 is fed from a controllable regulated voltage source 23. A change of the supply voltage produces an amplitude variation. The voltage supply source 23 is connected by conductors 24 and 25 with the operational amplifier 8 in the usual way. The conductors 24 and 25 are respectively connected to the voltage divider outputs of potentiometers 26 and 27 that themselves are connected across voltage sources 28 and 29.

The piezoelectric element is self-excited in this excitation circuit even when the elastic properties of the element change, for example as a result of temperature changes or aging of the material, so that the oscillator drive the element at the self-resonant frequency, either the fundamental or the harmonic thereof, in all cases. The resonant requirements do not change then if the impedance of the resonant element is changed by the application of voltages from the voltage source 22. The controllable voltage source 23 applied to the operational amplifier 8 makes possible a continuous amplitude variation.

The measurement signal determined by the contact potential difference between the oscillating electrode 1 and the counter-electrode 2 is supplied over a conductor 30 to a phase-sensitive amplifier 31 that is synchronized by a phase-reference signal provided by the excitation circuit through a signal conductor 32. The measurement signal is provided from the output of the phase-sensitive amplifier 31 to a signal processing circuit 33 that has its outputs connected with a registering device 34 for recording the measurement signal.

For an automatic zero balance the signal processing circuit 33 has a connection through a line 35 back to a voltage source 36 and therethrough to the reference or ground potential conductor 19. The voltage source 36 serves for compensation and for simulation of contact potential differences, as well as for calibration purposes.

A phase-stable reference signal is produced by the excitation circuit independently of resonant frequency and amplitude. The phase-sensitive amplifier does not need to be adjusted or tuned even when the resonance frequency changes as a result of a temperature change or aging of the piezoelectric material.

Although the invention has been disclosed with reference to a particular illustrated embodiment, it will be understood that modifications and variations are possible within the inventive concept.

We claim:

1. A piezoelectric transducer apparatus for measuring contact potentials between relatively movable electrodes and electron work function of surfaces and for atomar molecular and optical chopper applications, said apparatus having a piezoelectrically driven movable electrode and a counter-electrode, means for providing an oscillatory driving voltage for said movable electrodes, spring means for mounting said movable electrode and means for providing a controllable voltage superimposed on said oscillatory driving voltage for variation of the means spacing between said movable electrode and said counter-electrode, said movable electrode having first and second poles respectively on opposite sides of a position of said movable electrode to which said oscillatory driving voltage means provides said voltage to said movable electrode, said means for providing oscillatory driving voltage including a self excited oscillation generator circuit (8, 9, 13), having a reference or ground potential conductor (19), said apparatus further comprising a capacitor (20) connected between said first pole (5) of a piezoelectric driving element (4) of said movable electrode and said oscillation generator circuit;

a connection between said second pole (6) of said piezoelectric element and said reference or ground potential conductor;

connection means for applying said controllable voltage in parallel to said poles (5, 6) of said piezoelectric element, and an amplitude control circuit (26, 27, 28, 29) for varying the amplitude of said oscillatory driving voltage.

2. A piezoelectric transducer apparatus as defined in claim 1 in which said oscillation generation circuit comprises:

an operational amplifier (8) having an inverse feedback circuit (9) connected between the output (17) and the inverting input (16) of said amplifier and a positive feedback circuit (13) between said output (17) and the noninverting input of said amplifier, said capacitor (20) being connected between said first pole (5) of said piezoelectric element (4) and said inverting input (16) of said operational amplifier (8).

3. A piezoelectric transducer apparatus as defined in claim 2 in which a regulated controllable voltage source (23) is provided for said operational amplifier (8), the circuit for controlling said voltage constituting said circuit for varying the amplitude of said oscillatory driving voltage for said movable electrode.

* * * * *